(12) United States Patent
Chen et al.

(10) Patent No.: US 8,623,843 B2
(45) Date of Patent: Jan. 7, 2014

(54) ANTIMICROBIAL COMPOUND AND PREPARATION THEREOF

(75) Inventors: Shiguo Chen, Shenzhen (CN); Zaochuan Ge, Shenzhen (CN); Fei Xiao, Shenzhen (CN); Yangmiao Mo, Shenzhen (CN); Qianzhen Huang, Shenzhen (CN); Song Jiang, Shenzhen (CN)

(73) Assignee: Shenzhen University, Shenzhen (CN)

( * ) Notice: Subject to any disclaimer, the term of this patent is extended or adjusted under 35 U.S.C. 154(b) by 0 days.

(21) Appl. No.: 13/380,722

(22) PCT Filed: Apr. 7, 2010

(86) PCT No.: PCT/CN2010/071606
§ 371 (c)(1),
(2), (4) Date: Dec. 23, 2011

(87) PCT Pub. No.: WO2011/063625
PCT Pub. Date: Jun. 3, 2011

(65) Prior Publication Data
US 2012/0232301 A1    Sep. 13, 2012

(30) Foreign Application Priority Data

Nov. 28, 2009  (CN) .......................... 2009 1 0188570
Jan. 26, 2010  (CN) .......................... 2010 1 0116533

(51) Int. Cl.
*C07F 7/18*    (2006.01)
*A61K 33/00*   (2006.01)

(52) U.S. Cl.
USPC .......................................... 514/63; 556/413

(58) Field of Classification Search
USPC .............................................. 556/413
See application file for complete search history.

(56) References Cited

U.S. PATENT DOCUMENTS 5,936,703 A * 8/1999 Miyazaki et al. ........ 351/159.02

FOREIGN PATENT DOCUMENTS

| JP | 5-222064 A | 8/1993 |
| JP | 5-331455 A | 12/1993 |
| JP | 2008-239949 A | 10/2008 |
| WO | WO 2007/146680 | * 12/2007 | ............... B32B 5/16 |
| WO | WO 2007/146680 A1 | 12/2007 |

OTHER PUBLICATIONS

Ward et al., Antimicrobial Activity of Statistical Polymethacrylic Sulfopropylbetaines Against Gram-Positive and Gram-Negative Bacteria, Journal of Applied Polymer Science, 2006, pp. 1036-1041, vol. 101.
Madkour et al., Fast Disinfecting Antimicrobial Surfaces, Langmuir, 2009, pp. 1060-1067, vol. 25.
Saif et al., A Novel Application of Quaternary Ammonium Compounds as Anti Bacterial Hybrid Coating on Glass Surfaces. Langmuir, 2009 pp. 377-379, vol. 25.

* cited by examiner

*Primary Examiner* — Kamal Saeed
*Assistant Examiner* — Janet L Coppins
(74) *Attorney, Agent, or Firm* — Leason Ellis LLP.

(57) ABSTRACT

The present invention relates to the field of organic synthesis, and provides an organosilicon betaine type antimicrobial compound having a general formula I and preparation thereof:

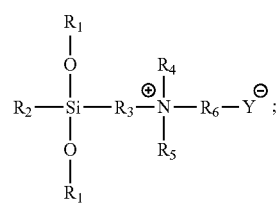

the antimicrobial compound provided by the present invention has a reactive functional group—siloxane, which can be subjected to chemical bonding with many material interfaces, thereby endowing a material or article surface treated with the antimicrobial compound I persistent antimicrobial activity. Also, the preparation of the compound has a simple process and easily controlled conditions, and is easy to be industrialized, which facilitates its wide applications.

18 Claims, No Drawings

ANTIMICROBIAL COMPOUND AND PREPARATION THEREOF

CROSS-REFERENCE TO RELATED PATENT APPLICATIONS

This application is a U.S. National Phase Application under 35 U.S.C. §371 of International Patent Application No. PCT/CN2010/071606, filed Apr. 7, 2010, and claims the benefit of Chinese Patent Application No. 200910188570.7, filed Nov. 28, 2009, and Chinese Patent Application No. 201010116533.8, filed Jan. 26, 2010, all of which are incorporated by reference herein. The International Application was published in Chinese on Jun. 3, 2011 as International Publication No. WO/2010/074115 under PCT Article 21(2).

FIELD OF THE INVENTION

The present invention relates to the field of organic synthesis, and more specifically to an antimicrobial compound and preparation thereof.

BACKGROUND OF THE INVENTION

Bacterial or fungal infection has become a worldwide important topic which poses a threat to human health and is given much attention in global medical and health services. It is one of important tools for dealing with bacterial or fungal infection to confer a material or article surface with antimicrobial property to prevent bacterial or fungal growth or multiplication thereon, even to kill bacteria or fungi on the surface. Now, internationally, antimicrobial materials can be divided into four main classes: (1) inorganic antimicrobial agents, for example, nano titanium dioxide, nano silver, nano copper, and their ions; (2) organic antimicrobial agents, for example, quaternary ammonium salts, thiazoles; (3) macromolecular antimicrobial agents, for example, macromolecular quaternary ammonium salts; and (4) natural antimicrobial agents and modifications thereof, for example, chitosan, sorbic acid.

It is the most common for conferring a material or article surface with antimicrobial property to apply a coating containing an antimicrobial agent (for example, nano silver, nano copper and their ions, or others) on the surface. The bacteriostasis or bactericidal effects of nano silver, nano copper, and other heavy metals and their ions are achieved by means of slow release of their metal ions into the environment. However, with usage time increasing, the antimicrobial activity of these materials gradually decreases, until it is eventually lost completely. In addition, microbial variation may be induced, resulting in an increase in the probability of drug resistance. Moreover, the harmfulness of nanomaterials is gradually being recognized and concerned. Organic antimicrobial agents and natural antimicrobial agents have poor heat resistance, which often limits their use ranges. Macromolecular quaternary ammonium salt antimicrobial agents are focused because they can overcome the shortcomings such as high volatility, difficulty in processing, and poor chemical stability of micromolecular antimicrobial agents, have excellent antimicrobial activity, and do not easily permeate into the human skin. For example, Ruowen Fu group [Reactive & functional polymers, 2007, 67:355-366] prepared a series of macromolecular quaternary ammonium salts of methacrylates as antimicrobial agent, having minimum inhibitory concentration (MIC) of 1.56-20 mg/mL. The polymeric antimicrobial agents are also mainly polymeric quaternary ammonium salts and polymeric haloamines, which have undesirable thermal stability. Moreover, in order to obtain a good antimicrobial agent, it is usually required that the antimicrobial agent is water-soluble. So, there is loss in these non-immobilized macromolecular antimicrobial agents, resulting in lack of durability in antimicrobial activity, and also putting a burden on the environment. For example, Lowe et al. [J. Appl. Polym. Sci., 2006, 101:1036-1041] prepared a series of polymeric betaine antimicrobial agents, having minimum inhibitory concentration (MIC) of 1125-2000 ug/mL, which provides a new thought to develop antimicrobial agents. But, they have no reactive functional group that can be immobilized, so that the disadvantage of loss due to release cannot be avoided.

The antimicrobial agent with such release property has at least two adverse factors: (1) the implanted antimicrobial agent has time-dependant release and is lack of persistent antimicrobial activity; (2) the released antimicrobial agent puts a burden on the environment. These factors cannot be neglected and it is inevitable to develop and prepare a green non-released antimicrobial agent. Immobilizing a group with antimicrobial activity onto a material or article surface through chemical bonding can confer the material or article with persistent antimicrobial activity, and also, would not cause contamination on the environment. Madkour [Langmuir, 2009, 25: 1060-1067] prepared a coating with rapid antimicrobial property by reacting a halogen-containing silane with a hydroxyl-containing surface and further employing atom transfer radical polymerization. However, this method has a complicated process and harsh conditions, and is difficult to be industrialized. Saif [Langmuir, 2009, 25:377-379] prepared an organosilicon quaternary ammonium salt antimicrobial agent having persistent antimicrobial activity, and DC-5700 early developed by DOW Corning also belongs to this class. But, the quaternary ammonium salt antimicrobial agent has poor heat resistance, limiting its use range.

It is a new requirement in the development of human society to research and develop a new class of durable antimicrobial agent that can be immobilized, by overcoming the disadvantages present in the field of current antimicrobial agents as described above.

SUMMARY OF THE INVENTION

One object of the present invention is to provide an antimicrobial compound, which can be tenaciously bonded to many material or product interfaces with a reactive function group (siloxane group) via chemical bonding made to generate persistent antimicrobial activity and hydrophilicity.

The organosilicon betaine type antimicrobial compound provided by the present invention has a general formula I:

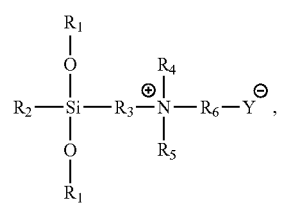

in which, $R_0$=H, $R_3X$;
$R_1$ is selected from —$CH_3$ or —$CH_2CH_3$;
$R_2$ is selected from —$OR_1$, —$CH_3$, or —$CH_2CH_3$;
$R_3$ is selected from —$(CH_2)_m NH(CH_2)_n$-, where m, n=1-6, or —$(CH_2)_p$-, where p=1-10;

$R_4$ is $-(CH_2)_qCH_3$, where q=0-17, or $R_4$=H;
$R_5$ is $-(CH_2)_qCH_3$, where q=0-17, or $R_5$=H;
$R_6$ is selected from $-(CH_2)_rNH(CH_2)_t$, where r, t=1-10, or $-(CH_2)_u$, where u=1-6;
Y is selected from $-COO$, or $-SO_3$.

In the general formula I, the substituents $R_4$ and $R_5$ are the same or different.

Another object of the present invention is to provide a method of preparing the antimicrobial compound, which has a simple synthesis process, easily controlled conditions, a high yield, and is easy to be industrialized.

This subject is achieved by a method of preparing the antimicrobial compound comprising the steps of:

preparing a tertiary amine-containing organic siloxane and continuously reacting the tertiary amine-containing organic siloxane with a reactant B by keeping in an environment at 10-80° C. with stirring for 1-48 h, to yield a white precipitate;

filtering or isolating by centrifugation the white precipitate, to yield an organosilicon betaine type antimicrobial compound, i.e. target product;

The reactant B is one selected from propane sultone, butane sultone, acrylic acid, β-propiolactone, $X(CH_2)_vSO_3^-$, or $X(CH_2)_vCO_2^-$, where X is Br, Cl or I, v is a positive integer greater than or equal to 1.

A typical synthetic route of the preparation method above is:

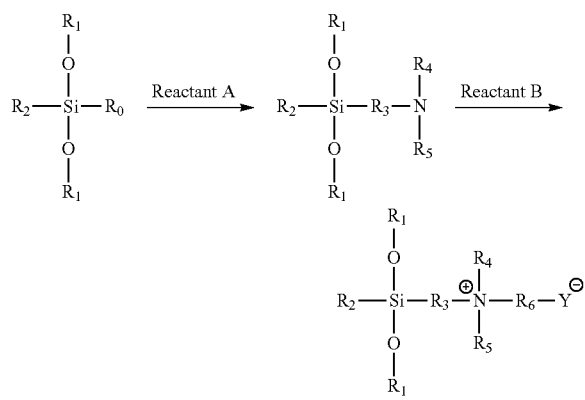

In the preparation steps above, the tertiary amine-containing organic siloxane is prepared by: reacting $(R_1O)_2R_2SiH$ with a reactant A by hydrosilylation at 10-80° C. in the presence of a platinum-based catalyst with stirring for 1-48 h; where $R_1$ is selected from $-CH_3$ or $-CH_2CH_3$, and $R_2$ is selected from $-OR_1$, $-CH_3$ or $-CH_2CH_3$; and the reactant A is a tertiary amine-containing alkene, preferably dimethylallylamine or diethylallylamine.

In the preparation steps above, the platinum-based catalyst is selected from chloroplatinic acid catalyst, $SiO_2$ supported platinum catalyst, activated carbon supported platinum catalyst, or Karstedt type platinum catalyst.

In the preparation steps above, the tertiary amine-containing organic siloxane can also be prepared by: reacting $(R_1O)_2R_2SiR_3X$ and $R_4R_5NH$ at 20-80° C. with a NaOH/isopropanol solution added as catalyst with stirring for 2-48 h; where $R_1$ is $-CH_3$ or $-CH_2CH_3$; $R_2$ is $-OR_1$, $-CH_3$ or $-CH_2CH_3$; $R_3$ is selected from $-(CH_2)_p$, where p=1-10; $R_4$ is $-(CH_2)_qCH_3$, where q=0-17; $R_5$ is $-(CH_2)_qCH_3$, where q=0-17; X is Br, Cl or I.

The present invention also provides another method of preparing the antimicrobial compound, comprising the step of: continuously reacting an amino-containing siloxane with a reactant B by keeping in an environment at 10-80° C. with stirring for 1-48 h to yield an organosilicon betaine type antimicrobial compound, i.e. target product.

Similarly, the reactant B is one selected from propane sultone, butane sultone, acrylic acid, β-propiolactone, $X(CH_2)_vSO_3^-$, or $X(CH_2)_vCO_2^-$, where X is Br, Cl or I, v is a positive integer greater than or equal to 1.

The advantages of the technical solutions above is in that the antimicrobial compound has a reactive functional group—siloxane, which can be subjected to chemical bonding with many material interfaces, thereby rendering a material or article surface treated with the antimicrobial compound persistent antimicrobial activity and stronger hydrophilicity. Also, the preparation method has a simple synthesis process and easily controlled conditions, and is easy to be industrialized, which facilitates its wide applications. In addition, the antimicrobial compound has unique advantages such as resistance to acids, alkalis and salts, especially low toxicity and good chemical stability and thermal stability, so that an article surface treated with the antimicrobial compound can be subjected to various common disinfection treatments.

DETAILED DESCRIPTION OF THE INVENTION

In order to make the above objects, technical solutions and advantages of the invention more apparent, the present invention will be further described in detail below in conjunction with embodiments. It should be understood that the specific embodiments described herein are only intended to explain the present invention and not to limit the present invention.

Embodiment 1

98.6 g triethoxysilane [$(CH_3CH_2O)_3SiH$] was weighted and added to a round-bottomed flask with mechanical stirring and a reflux apparatus. After 0.2 ml of chloroplatinic acid/isopropanol catalyst was added, 51.2 g dimethylallylamine [$CH_2=CHCH_2N(CH_3)_2$] was slowly added dropwise via a dropping funnel with stirring at 60° C. After the dropwise addition was completed, the reaction was continued for 1 h. The temperature was reduced to 50° C., and then 73.2 g propane sultone [

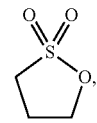

hereafter referred to simply as 1,3-PS] (dissolved in 400 mL absolute ethanol) was added dropwise. After the dropwise addition was completed, the reaction was continued for 1 h, to yield a white precipitate. The precipitate was isolated by centrifugation and purified several times, to yield an organosilicon-sulfonic acid type betaine antimicrobial agent, with the structural formula: $(CH_3CH_2O)_3Si(CH_2)_3{}^+N(CH_3)_2(CH_2)_3SO_3^-$, and having a minimum inhibitory concentration (MIC) of 15 mg/mL and a minimum bactericidal concentration (MEC) of 20 mg/mL for both *E. coli* (8099) and *S. aureas* (ATCC6538).

Embodiment 2

107.8 g methyldiethoxysilane [$(CH_3CH_2O)_2CH_3SiH$] was weighted and added to a flat-bottomed flask with magnetic stirring and a reflux apparatus. After 0.25 g $SiO_2$ supported platinum-gold catalyst was added, 88.9 g diethylallylamine [$CH_2$=$CHCH_2N(CH_2CH_3)_2$] was slowly added dropwise via a dropping funnel with magnetic stirring at 30° C., and the reaction time was started. After 8 h of reaction, the catalyst was recovered by filtration under reduced pressure. Then, the filtrate was collected, to which 97.6 g 1,3-PS (dissolved in 400 mL absolute ethanol) was added dropwise. The reaction was continued at 30° C. for 10 h, to yield a white precipitate. The precipitate was filtered and purified by washing with ethanol several times, to yield an organosilicon-sulfonic acid type betaine antimicrobial agent, with the structural formula: $(CH_3CH_2O)_2SiCH_3(CH_2CH_3)_3{}^+N(CH_3)_2(CH_2)_3SO_3{}^-$, and having a MIC of 25 mg/mL and a MBC of 30 mg/mL for both E. coli (8099) and S. aureas (ATCC6538).

Embodiment 3

107.6 g methyldiethoxysilane [$(CH_3CH_2O)_2CH_3SiH$] was weighted and added to a flat-bottomed flask with magnetic stirring and a reflux apparatus. After 0.20 g of Karstedt type platinum-gold catalyst was added, 68.2 g dimethylallylamine [$CH_2$=$CHCH_2N(CH_3)_2$] was slowly added dropwise via a dropping funnel with magnetic stirring at 20° C., and the reaction time was started. After 24 h of reaction, the catalyst was recovered by filtration under reduced pressure. Then, the filtrate was collected, to which 93.2 g sodium chloroacetate [$ClCH_2CO_2Na$] (dissolved in 400 mL absolute ethanol) was added dropwise. The reaction was continued at 20° C. for 24 h, to yield a white precipitate. The precipitate was isolated by centrifugation and purified several times, to yield an organosilicon carboxylic acid type betaine antimicrobial agent, with the structural formula: $(CH_3CH_2O)_2SiCH_3(CH_2)_3{}^+N(CH_3)_2CH_2CO_2{}^-$, and having a MIC of 20 mg/mL and a MBC of 25 mg/mL for both E. coli (8099) and S. aureas (ATCC6538).

Embodiment 4

107.6 g methyldiethoxysilane [$(CH_3CH_2O)_2CH_3SiH$] was weighted and added to a round-bottomed flask with mechanical stirring and a reflux apparatus. After 0.20 g activated carbon supported platinum-gold catalyst was added, 68.2 g dimethylallylamine [$CH_2$=$CHCH_2N(CH_3)_2$] was slowly added dropwise via a dropping funnel with stirring at 50° C. After the dropwise addition was completed, the reaction was continued for 2 h. The catalyst was recovered by filtration under reduced pressure. Then, the filtrate was collected, to which 57.7 g β-propiolactone

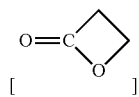

(dissolved in 400 mL butanone) was added dropwise. The reaction was continued for 6 h at 40° C., to yield a white precipitate. The precipitate was isolated by centrifugation and purified several times, to yield an organosilicon carboxylic acid type betaine antimicrobial agent, with the structural formula: $(CH_3CH_2O)_2SiCH_3(CH_2)_3{}^+N(CH_3)_2(CH_2)_2CO_2{}^-$, and having a MIC of 10 mg/mL and a MBC of 20 mg/mL for both E. coli (8099) and S. aureas (ATCC6538).

Embodiment 5

142.5 g N,N-diethyl-3-aminopropyltrimethoxysilane [$(CH_3CH_2)_2N(CH_2)_3Si(OCH_3)_3$] was weighted and added to a flat-bottomed flask with magnetic stirring and a reflux apparatus. 73.2 g 1,3-PS (dissolved in 400 mL acetone) was slowly added dropwise with magnetic stirring. The reaction was continued for 48 h at 10° C., to yield a white precipitate. The precipitate was isolated by centrifugation and purified several times, to yield an organosilicon sulfonic acid type betaine antimicrobial agent, with the structural formula: $(CH_3O)_3Si(CH_2)_3{}^+N(CH_2CH_3)_2(CH_2)_3SO_3{}^-$, and having a MIC of 15 mg/mL and a MBC of 20 mg/mL for both E. coli (8099) and S. aureas (ATCC6538).

Embodiment 6

97.8 g trimethoxysilane [$HSi(OCH_3)_3$] was weighted and added to a flat-bottomed flask with mechanical stirring and a reflux apparatus. After 0.20 g activated carbon supported platinum-gold catalyst was added, 88.9 g diethylallylamine [$CH_2$=$CHCH_2N(CH_2CH_3)_2$] was slowly added dropwise via a dropping funnel with magnetic stirring at 50° C. After the dropwise addition was completed, the reaction was continued for 2 h. The heating was stopped, and the catalyst was recovered by filtration under reduced pressure. Then, the filtrate was collected, to which 93.2 g $ClCH_2CH_2SO_3Na$ (dissolved in 400 mL absolute ethanol) was added dropwise. The mixture was heated to 50° C. and further reacted for 10 h, to yield a white precipitate. The precipitate was filtered and purified by washing with absolute ethanol several times, to yield an organosilicon sulfonic acid type betaine antimicrobial agent, with the structural formula: $(CH_3O)_3Si(CH_2)_3{}^+N(CH_2CH_3)_2(CH_2)_2SO_3{}^-$, and having a MIC of 20 mg/mL and a MBC of 25 mg/mL for both E. coli (8099) and S. aureas (ATCC6538).

Embodiment 7

124.0 g N-(β-aminoethyl)-γ-aminopropylmethyldimethoxysilane [$NH_2(CH_2)_2NH(CH_2)_3SiCH_3(OCH_3)_2$] was weighted and added to a flat-bottomed flask with a magnetic stirrer and a reflux apparatus. 73.2 g 1,3-PS (dissolved in 400 mL absolute ethanol) was slowly added dropwise with magnetic stirring. The mixture was heated to 40° C. and reacted for 2 h, to yield an organosilicon sulfonic acid type betaine antimicrobial agent as yellowish oil, with the structural formula: $(CH_3O)_3Si(CH_2)_3NH(CH_2)_2{}^+NH_2(CH_2)_3SO_3{}^-$, and having a MIC of 25 mg/mL and a MEC of 30 mg/mL for both E. coli (8099) and S. aureas (ATCC6538).

Embodiment 8

119.2 g chloropropyltrimethoxysilane [$(CH_3O)_3SiCH_2CH_2CH_2Cl$] was weighted and added to a round-bottomed flask with a mechanical stirrer and a reflux apparatus. 60.7 g di-n-propylamine [$(CH_3CH_2CH_2)_2NH$] (dissolved in 200 ml absolute ethanol) was slowly added dropwise via a dropping funnel with stirring at 80° C. After the dropwise addition was completed, the reaction was continued for 10 h, and then the temperature was reduced to 30° C. 73.2 g 1,3-PS (dissolved in 200 mL absolute ethanol) was added dropwise. The reaction was continued for 10 h, to yield a white precipitate. The precipitate was isolated by centrifugation and purified several times, to yield an organosilicon sulfonic acid type betaine antimicrobial agent, with the structural formula: $(CH_3O)_3Si(CH_2)_3{}^+N(CH_2CH_2CH_3)_2(CH_2)_3SO_3{}^-$, and having a MIC of 15 mg/mL and a MBC of 20 mg/mL for both E. coli (8099) and S. aureas (ATCC6538).

The resulting products from the above examples were used for treating a glass surface respectively, a superhydrophilic surface at a contact angle of less than 10° C. was all obtained. In addition, they were tested for antimicrobial activity and persistent antimicrobial activity using the colony counting method, and the results are shown in table 1.

TABLE 1

Analysis of persistent antimicrobial activity of antimicrobial agents in embodiments 1-8 (plate counting method)

| Sample | Strain | Wash times | | | | |
|---|---|---|---|---|---|---|
| | | 0 | 1 | 5 | 10 | 30 |
| Embodiment 1 | E. coli | 99.9% | 99.8% | 99.5% | 99.0% | 99.2% |
| | S. aureas | 99.9% | 99.9% | 99.6% | 99.5% | 99.0% |
| Embodiment 2 | E. coli | 99.9% | 99.9% | 99.3% | 98.9% | 98.5% |
| | S. aureas | 99.9% | 99.9% | 99.9% | 99.6% | 99.0% |
| Embodiment 3 | E. coli | 99.9% | 99.8% | 99.2% | 97.9% | 97.2% |
| | S. aureas | 99.9% | 99.9% | 99.5% | 98.2% | 97.6% |
| Embodiment 4 | E. coli | 99.9% | 99.8% | 99.0% | 98.6% | 98.1% |
| | S. aureas | 99.9% | 99.9% | 99.6% | 98.9% | 98.3% |
| Embodiment 5 | E. coli | 99.9% | 99.7% | 99.0% | 98.7% | 98.0% |
| | S. aureas | 99.9% | 99.9% | 99.5% | 98.8% | 98.2% |
| Embodiment 6 | E. coli | 99.9% | 99.8% | 99.3% | 97.9% | 97.2% |
| | S. aureas | 99.9% | 99.9% | 99.5% | 98.2% | 97.6% |
| Embodiment 7 | E. coli | 99.9% | 99.5% | 99.1% | 98.6% | 98.0% |
| | S. aureas | 99.9% | 99.8% | 99.6% | 99.1% | 98.2% |
| Embodiment 8 | E. coli | 99.9% | 99.7% | 99.3% | 98.7% | 98.2% |
| | S. aureas | 99.9% | 99.9% | 99.5% | 98.8% | 98.5% |

In other preferred embodiments of the present invention, an equivalent amount of substance of $CH_3CH_2(CH_3O)_2SiH$, $CH_3CH_2(CH_3CH_2O)_2SiH$, $CH_3(CH_3O)_2SiH$ can be selected in place of $(CH_3CH_2O)_3SiH$ or $(CH_3O)_3SiH$ or $(CH_3CH_2O)_2CH_3SiH$; also, an equivalent amount of substance of butane sultone, acrylic acid, $X(CH_2)_vSO_3Na$, or $X(CH_2)_vCO_2Na$ (where X is Br, Cl or I; v is a positive integer greater than or equal to 1) can be selected in place of propane sultone, β-propiolactone, $ClCH_2CO_2Na$, or $ClCH_2CH_2SO_3Na$.

The descriptions above are only several embodiments of the present invention, which are described specifically and in detail, and therefore, these cannot be construed as limiting the scope of the present invention. It should be noted that other many modifications and improvements can be made by one skilled in the art, without departing from the concept of the present invention, and such modifications and improvements fall into the scope of the present invention.

The invention claimed is:

1. An organosilicon betaine type antimicrobial compound, having a general formula I:

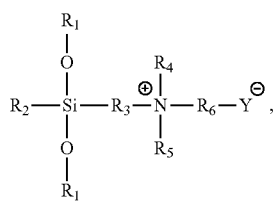

wherein, $R_1$ is selected from the group consisting of —$CH_3$ and —$CH_2CH_3$;

$R_2$ is —$CH_3$;

$R_3$ is selected from the group consisting of —$(CH_2)_mNH(CH_2)_n$, wherein m, n=1-6, and —$(CH_2)_p$, wherein p=1-10;

$R_4$ is selected from the group consisting of —$(CH_2)_qCH_3$, wherein q=1-17; and —H $R_5$ is selected from the group consisting of —$(CH_2)_qCH_3$, wherein q=1-17; and —H $R_6$ is selected from the group consisting of —$(CH_2)_rNH(CH_2)_t$, wherein r, t=1-10, and —$(CH_2)_u$, wherein u=1-6; and Y is selected from the group consisting of —COO, and —$SO_3$.

2. The antimicrobial compound according to claim 1, wherein in the general formula I, the substituents $R_4$ and $R_5$ are the same.

3. A method of preparing the antimicrobial compound according to claim 1, comprising the steps of:

preparing a tertiary amine-containing organic siloxane and continuously reacting the tertiary amine-containing organic siloxane with a reactant B by keeping in an environment at 10-80° C. with stirring for 1-48 hours, to yield a white precipitate; and filtering or purifying the white precipitate by centrifugation, to yield an organosilicon betaine type antimicrobial compound, i.e. target product, wherein the reactant B is selected from the group consisting of propane sultone, butane sultone, acrylic acid, β-propiolactone, $X(CH_2)_vSO_3^-$, and $X(CH_2)_vCO_2^-$, wherein X is Br, Cl or I, and v is a positive integer greater than or equal to 1.

4. The method of preparing the antimicrobial compound according to claim 3, wherein the tertiary amine-containing organic siloxane is prepared by reacting $(R_1O)_2R_2SiH$ with a reactant A by hydrosilylation at 10-80° C. in the presence of a platinum-based catalyst with stirring for 1-48 hours.

5. The method of preparing the antimicrobial compound according to claim 4, wherein the reactant A is a tertiary amine-containing alkene, preferably dimethylallylamine or diethylallylamine.

6. The method of preparing the antimicrobial compound according to claim 4, wherein the platinum-based catalyst is selected from the group consisting of chloroplatinic acid catalyst, $SiO_2$ supported platinum catalyst, activated carbon supported platinum catalyst, and Karstedt type platinum catalyst.

7. The method of preparing the antimicrobial compound according to claim 3, wherein the tertiary amine-containing organic siloxane is prepared by reacting $(R_1O)_2 R_2SiR_3X$ and $R_4R_5NH$ at 20-80° C. with a NaOH/isopropanol solution added as catalyst with stirring for 2-48 hours; wherein $R_1$ is selected from the group consisting of —$CH_3$ and —$CH_2CH_3$;

$R_3$ is —$(CH_2)_p$, wherein p=1-10;

$R_4$ is —$(CH_2)_qCH_3$, wherein q=1-17; and $R_5$ is —$(CH_2)_qCH_3$, wherein q=1-17.

8. A method of preparing the antimicrobial compound according to claim 1, comprising the step of:

continuously reacting an amino-containing siloxane with a reactant B by keeping in an environment at 10-80° C. with stirring for 1-48 hours to yield an organosilicon betaine type antimicrobial compound, i.e. target product; wherein the reactant B is selected from the group consisting of propane sultone, butane sultone, acrylic acid, β-propiolactone, $X(CH_2)_vSO_3^-$, and $X(CH_2)_vCO_2^-$, wherein X is Br, Cl or I, and v is a positive integer greater than or equal to 1.

9. The antimicrobial compound according to claim 1, wherein in the general formula I, the substituents $R_4$ and $R_5$ are different.

10. A method of preparing the antimicrobial compound according to claim 2, comprising the steps of:
preparing a tertiary amine-containing organic siloxane and continuously reacting the tertiary amine-containing organic siloxane with a reactant B by keeping in an environment at 10-80° C. with stirring for 1-48 hours, to yield a white precipitate; and
filtering or purifying the white precipitate by centrifugation, to yield an organosilicon betaine type antimicrobial compound, i.e. target product, wherein
the reactant B is one selected from the group consisting of propane sultone, butane sultone, acrylic acid, β-propiolactone, $X(CH_2)_vSO_3^-$, and $X(CH_2)_vCO_2^-$, wherein X is Br, Cl or I, and v is a positive integer greater than or equal to 1.

11. A method of preparing the antimicrobial compound according to claim 2, comprising the step of:
continuously reacting an amino-containing siloxane with a reactant B by keeping in an environment at 10-80° C. with stirring for 1-48 hours to yield an organosilicon betaine type antimicrobial compound, i.e. target product; wherein
the reactant B is selected from the group consisting of propane sultone, butane sultone, acrylic acid, β-propiolactone, $X(CH_2)_vSO_3^-$, and $X(CH_2)_vCO_2^-$, wherein X is Br, Cl or I, and v is a positive integer greater than or equal to 1.

12. An organosilicon betaine type antimicrobial compound, having a general formula I:

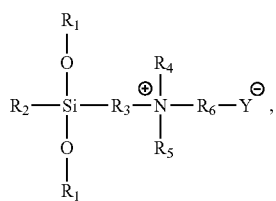

wherein,
$R_1$ is selected from the group consisting of —$CH_3$ and —$CH_2CH_3$;
$R_2$ is selected from the group consisting of —$OR_1$, and —$CH_3$;
$R_3$ is —$(CH_2)_3NH(CH_2)_2$;
$R_4$ is selected from the group consisting of —$(CH_2)_qCH_3$, wherein q=0-17; and —H;
$R_5$ is selected from the group consisting of —$(CH_2)_qCH_3$, wherein q=0-17; and —H;
$R_6$ is selected from the group consisting of —$(CH_2)_rNH(CH_2)_t$, wherein r, t=1-10, and —$(CH_2)_u$, wherein u=1-6; and Y is selected from the group consisting of —COO, and —$SO_3$.

13. A method of preparing the antimicrobial compound according to claim 12, comprising the steps of:
preparing a tertiary amine-containing organic siloxane and continuously reacting the tertiary amine-containing organic siloxane with a reactant B by keeping in an environment at 10-80° C. with stirring for 1-48 hours, to yield a white precipitate; and
filtering or purifying the white precipitate by centrifugation, to yield an organosilicon betaine type antimicrobial compound, i.e. target product, wherein
the reactant B is selected from the group consisting of propane sultone, butane sultone, acrylic acid, β-propiolactone, $X(CH_2)_vSO_3^-$, and $X(CH_2)_vCO_2^-$, wherein X is Br, Cl or I, and v is a positive integer greater than or equal to 1.

14. The method of preparing the antimicrobial compound according to claim 13, wherein the tertiary amine-containing organic siloxane is prepared by reacting $(R_1O)_2R_2SiH$ with a reactant A by hydrosilylation at 10-80° C. in the presence of a platinum-based catalyst with stirring for 1-48 hours.

15. The method of preparing the antimicrobial compound according to claim 14, wherein the reactant A is a tertiary amine-containing alkene, preferably dimethylallylamine or diethylallylamine.

16. The method of preparing the antimicrobial compound according to claim 14, wherein the platinum-based catalyst is selected from the group consisting of chloroplatinic acid catalyst, $SiO_2$ supported platinum catalyst, activated carbon supported platinum catalyst, and Karstedt type platinum catalyst.

17. The method of preparing the antimicrobial compound according to claim 13, wherein the tertiary amine-containing organic siloxane is prepared by reacting $(R_1O)_2R_2SiR_3X$ and $R_4R_5NH$ at 20-80° C. with a NaOH/isopropanol solution added as catalyst with stirring for 2-48 hours; wherein
$R_4$ is —$(CH_2)_qCH_3$, wherein q=0-17; and
$R_5$ is —$(CH_2)_qCH_3$, wherein q=0-17.

18. A method of preparing the antimicrobial compound according to claim 12, comprising the step of:
continuously reacting an amino-containing siloxane with a reactant B by keeping in an environment at 10-80° C. with stirring for 1-48 hours to yield an organosilicon betaine type antimicrobial compound, i.e. target product; wherein
the reactant B is selected from the group consisting of propane sultone, butane sultone, acrylic acid, β-propiolactone, $X(CH_2)_vSO_3^-$, and $X(CH_2)_vCO_2^-$, wherein X is Br, Cl or I, and v is a positive integer greater than or equal to 1.

* * * * *